United States Patent
Fine (10) Patent No.: US 6,400,972 B1
(45) Date of Patent: Jun. 4, 2002

(54) NON-INVASIVE METHOD AND SYSTEM OF OPTICAL MEASUREMENTS FOR DETERMINING THE CONCENTRATION OF A SUBSTANCE IN BLOOD

(75) Inventor: Ilya Fine, Rehovot (IL)

(73) Assignee: Orsense Ltd., Tirat Hacarmel (IL)

(*) Notice: Subject to any disclaimer, the term of this patent is extended or adjusted under 35 U.S.C. 154(b) by 0 days.

(21) Appl. No.: 09/468,178

(22) Filed: Dec. 21, 1999

Related U.S. Application Data (63) Continuation of application No. PCT/IL99/00331, filed on Jun. 16, 1999.

(30) Foreign Application Priority Data

Jun. 17, 1998 (IL) ................................................ 124965

(51) Int. Cl.⁷ ................................................ A61B 5/00
(52) U.S. Cl. ........................ 600/322; 600/310; 600/335
(58) Field of Search ................................ 600/309–310, 600/322–324, 326, 328, 330, 335, 316, 334–336, 363, 365, 344

(56) References Cited

U.S. PATENT DOCUMENTS

| | | | |
|---|---|---|---|
| 3,412,729 A | | 11/1968 | Smith, Jr. |
| 4,463,762 A | | 8/1984 | Rubens |
| 4,714,341 A | | 12/1987 | Hamaguri et al. ............. 356/41 |
| 4,786,394 A | * | 11/1988 | Enzer et al. ................. 204/401 |
| 4,883,055 A | | 11/1989 | Merrick |
| 4,927,264 A | | 5/1990 | Shiga et al. ................... 356/41 |
| 4,975,581 A | * | 12/1990 | Robinson et al. ...... 250/339.09 |
| 5,054,487 A | * | 10/1991 | Clarke ......................... 600/316 |
| 5,069,214 A | * | 12/1991 | Samaras et al. ............. 600/323 |
| 5,111,817 A | * | 5/1992 | Clark et al. .................. 600/323 |
| 5,282,467 A | * | 2/1994 | Piantadosi et al. .......... 600/335 |
| 5,638,816 A | | 6/1997 | Kiani-Azarbayjany et al. |
| 5,827,181 A | * | 10/1998 | Dias et al. ................... 600/322 |
| 5,931,779 A | | 8/1999 | Arakaki et al. ............. 600/310 |

FOREIGN PATENT DOCUMENTS

| | | |
|---|---|---|
| EP | 0 227 119 | 12/1986 |
| WO | WO 98/17174 | 4/1998 |
| WO | WO 00/09004 | 2/2000 |

OTHER PUBLICATIONS

Linderberg, Walter and Jan–Ake Persson. "Partial Least –Square Method for Spectrofluorimetric Analysis of Mixtures of Humic Acid and Ligninsulfonte" Analytical Chemistry, vol. LV, p. 643–647 (1983).*

Earl H. Wood et al., "Photoelectric Determination of Arterial Oxygen Saturation in Man", Journal of Laboratory and Clinical Medicine, vol. 34, No. 1, Jun. 1949, pp. 387–401, XP002114776.

International Search Report dated Sep. 8, 2000 from the International Searching Authority for International Application Number PCT/IL99/00694.

* cited by examiner

*Primary Examiner*—Eric F. Winakur
*Assistant Examiner*—Matthew Kremer
(74) *Attorney, Agent, or Firm*—Fitch, Even, Tabin & Flannery (57) ABSTRACT

An over-systolic pressure is applied to a patient's blood perfused fleshy medium. The pressure causes a state of temporary blood flow cessation within a time period insufficient for irreversible changes in the fleshy medium. Release of the over systolic pressure causes a state of transitional blood flow terminating with the normal blood flow. At least two sessions of measurement, separated in time, are executed and at least one of these sessions is selected within the time period including the state of temporary blood flow cessation and the state of transitional blood flow. Optical non-invasive measurement of the concentration of at least one blood constituent are successively performed at these at least two sessions, and respective values of the concentration are obtained.

25 Claims, 5 Drawing Sheets

NON-INVASIVE METHOD AND SYSTEM OF OPTICAL MEASUREMENTS FOR DETERMINING THE CONCENTRATION OF A SUBSTANCE IN BLOOD

This application is a continuation of PCT/L99/00331 filed Jun. 16, 1999.

FIELD OF THE INVENTION

This invention in is the field of non-invasive optical measuring techniques and relates to a method for determining the concentration of a substance in the patient's blood, such as glucose, hemoglobin, drugs or cholesterol.

BACKGROUND OF THE INVENTION

Optical methods of determining the chemical composition of blood include spectrophotometric measurements which enable the indication of the presence of various blood constituents based on known spectral behaviors of these constituents. These spectrophotometric measurements may be effected either in vitro or in vivo. The measurements in vitro are invasive, i.e. require a blood sample to be physically withdrawn and investigated. At present, these measurements have become unpopular, due to the increasing danger of infection.

The non-invasive optical measurements in vivo may be briefly divided into two main groups based on different methodological concepts. The first group represents a so-called "DC measurement technique", and the second group is called "AC measurement technique".

According to the DC measurement technique, any desired location of a blood perfused tissue is illuminated by the light of a predetermined spectral range, and the tissue reflection and/or transmission effect is studied. Notwithstanding the fact that this technique provides a relatively high signal-to-noise ratio, the results of such measurements depend on all the spectrally active components of the tissue (i.e. skin, blood, muscles, fat, etc.), and therefore they need to be further processed to separate the "blood signals" from the detected signals. Moreover, proportions of the known components vary from person to person and from time to time. To resolve this problem, a calibration must periodically be provided, which constitutes an invasive blood test and therefore renders the DC technique of optical measurements to be actually invasive.

The AC measurement technique focuses on measuring only the "blood signal" of a blood perfused tissue illuminated by a predetermined range of wavelengths. To this end, what is actually measured is a time-dependent component only of the total light reflection or light transmission signal obtained from the tissue.

A typical example of the AC measurement technique is a known method of pulse oximetry, wherein a pulsatile component of the optical signal obtained from a blood perfused tissue is utilized for determining the arterial blood oxygen saturation. In other words, the difference in light absorption of the tissue measured during the systole and the diastole is considered to be caused by blood that is pumped into the tissue during the systole phase from arterial vessels and therefore has the same oxygen saturation as in the central arterial vessels. Not only can the oxygen saturation be determined, but in a similar way, concentrations of other chemical elements in the arterial blood can be determined.

The major drawback of such an AC measurement technique is its relatively low signal-to-noise ratio, as compared to that of the DC measurement technique, especially in cases where an individual has a poor cardiac output, insufficient for providing a pulsatile signal suitable for accurate measurements.

Various methods have been suggested to enhance the natural pulsatile signal of an individual for effecting non-invasive optical measurements.

U.S. Pat. No. 4,883,055 discloses a method and device for artificially inducing blood pulse for use with a pulse oximeter. A cuff wrapped around a body member having an artery upstream from a testing site is adapted for applying a squeezing pulse to the body member, the squeezing pulse being synchronized with a normal blood pulse. Oxygen saturation in the arterial blood is determined based on spectrophotometric non-invasive measurements, which are effected according to the general approach of the above-mentioned AC technique.

U.S. Pat. No. 4,927,264 discloses a non-invasive apparatus and a method for measuring blood constituents in venous blood. The venous blood stream is made time-variant by applying pressure with a peak value of the minimum blood pressure to a proximal portion from a measuring part.

U.S. Pat. No. 5,638,816 discloses a blood glucose monitoring system, which provides for inducing an active pulse in the blood volume of a patient according to a predictable cyclic pattern. The induction of an active pulse causes a cyclic change in the flow of arterial blood through a fleshy medium under the test. By actively inducing a change of the blood volume, modulation of the volume of blood can be obtained to provide a greater signal-to-noise ratio. This enables constituents in blood to be detected at concentration levels below those previously detectable in a non-invasive system. Radiation which passes through the fleshy medium is sensed by a detector which generates a signal indicative of the intensity of the detected radiation. Signal processing is performed on the electrical signal to separate those optical characteristics of the electrical signal which are associated with the optical characteristics of the blood.

The techniques disclosed in the above patents use the artificially induced volumetric changes of either arterial or venous blood. Since each of these techniques is specific about the kind of blood under test, they all impose severe restrictions on a value of the artificially applied pressure. This is due to different "disturbing pressure values" allowed for different kinds of blood flow. It means that for each kind of blood flow, there is a pressure value that disturbs specifically this kind of flow much more than any other kind. For example, when the artificial pressure at a value of 60 mmHg is applied to a proximal body part, the venous blood flow will be affected, whereas the arterial blood flow will not be affected, since the individual's diastolic pressure is usually higher than 60 mmHg. The applied artificial pressure definitely should not exceed pressures causing substantial deformation of the tissue, since only blood flow changes are supposed to be detected by optical measurements, and the measurements are to be effected in synchronism with the artificial pulse. However, if such an artificially induced pulse causes uncontrollable changes of the optical properties of the tissue, these changes cannot be distinguished from those caused by the blood flow fluctuations which are the target of the measurements.

SUMMARY OF THE INVENTION

There is accordingly a need in the art to facilitate non-invasive, optical measurements of the chemical composition of blood, by providing a novel method combining advantages of both the DC and AC techniques of optical measurements with a high signal-to-noise ratio.

The main idea of the present invention is based on the fact that the light response characteristics (i.e., absorption and/or scattering) of a blood perfused medium dramatically changes when a character of blood flow changes. It has been found by the inventors, that the optical characteristics of a blood perfused fleshy medium (e.g., the patient's finger) start to change in time, when causing blood flow cessation. In other words, once the blood flow cessation state is established, the optical characteristics start to change dramatically, such that they differ from those of the fleshy medium with a normal blood flow by about 25 to 45%, and sometimes even by 60%.

Hence, the accuracy (i.e., signal-to-noise ratio) of the optical measurements can be substantially improved by taking at least two timely separated measurement sessions each including at least two measurements with different wavelengths of incident radiation. The light response of the medium at these two sessions essentially differ from each other. At least one of the measurement sessions during which the measurement is effected should be chosen either during temporary blood flow cessation, or during the state of transitional blood flow.

In the inventive method, it is therefore suggested to distinguish the normal blood flow from the state of temporary blood cessation by detecting that at least one optical characteristic associated with light absorption and/or scattering of the blood has varied by a predetermined threshold value, and that the character of its change corresponds to the behavior of a time-dependent function. Since variations in the light absorption and/or scattering of blood affect both its light transmitting and light reflecting properties, this at least one detected optical characteristic may constitute either the light transmission or the light reflection of the blood perfused medium.

There is thus provided according to the invention, a non-invasive method of optical measurements for determining the concentration of at least one substance in patient's blood, the method comprising the steps of:

(a) applying an over-systolic pressure to the patient's blood perfused fleshy medium with a normal blood flow, so as to cause a state of temporary blood flow cessation for a cessation time period being insufficient for irreversible changes in the fleshy medium;

(b) releasing the over systolic pressure to cause a state of transitional blood flow terminating with the normal blood flow;

(c) selecting at least two timely separated sessions of the optical measurements on the blood perfused fleshy medium such that light response of the medium at said at least two sessions substantially differs from each other, wherein at least one of said at least two sessions is selected within a time period including the state of temporary blood flow cessation and the state of transitional blood flow;

(d) effecting the measurements at said at least two sessions successively, each session including at least two measurements with different wavelengths of incident light; and (e) determining for each of said at least two sessions a corresponding value of the concentration of said at least on substrate, analyzing the determined values and obtaining a corrected value of said concentration.

It is, of course, possible that both of the at least two sessions of measurements are selected to be between the initially existed and the finally established normal blood flow states, namely during the period of time including the state of temporary blood flow cessation and the state of transitional blood flow. However, one of these at least two sessions may be selected at a state of the normal blood flow.

The blood subjected to the optical test comprises arterial, venous and capillary components. The blood is temporarily "stagnated" in the fleshy medium when the over-systolic pressure is applied, and freely flows through the medium when the pressure is released. Values of the concentrations so obtained should thus be considered more meaningful, as compared to those obtained with the known techniques based on the measurement focused on either the arterial or venous blood component.

By its nature, the method of the present invention is simple and ensures a relatively high signal-to-noise ratio, as compared to the methods utilizing measurements synchronized with the blood pulse. This is owing to the fact that the present invention enables the parameters of the unchanged blood sample to be determined by using two or more readings of significantly distinct amplitudes.

Such an approach has not ever been used or suggested in the prior art. This is actually an advantageous combination of the principles of DC- and AC-techniques. Indeed, on the one hand, owing to high amplitude(s) of the light transmission or reflection signal obtained during the artificially created newly suggested blood flow states, the method resembles the DC-techniques. On the other hand, the method is based on processing the differences between readings of at least two measurements, which is generally similar to the conventional AC-techniques. This method is also advantageous since it is less dependent on motional or other non blood-related artifacts.

As indicated above, the optical characteristics of a blood perfused fleshy medium at the state of blood flow cessation differ from those of the fleshy medium with normal blood flow by about 25 to 45%, and sometimes even by 60%. Conventional methods of pulse oximetry make use of fluctuations of light transmitting characteristics in the range of about 2%. A threshold difference of about 5% between two measurements taken according to the inventive method will fairly satisfy the purpose, namely the concentration determined on the basis of such two measurements will already ensure much more reliable results than those which might be obtained by the pulse oximety technique.

Since the novel method enables to obtain a spectrum of readings differing from each other by up to 60%, more than two sessions may be chosen for effecting the measurements and for further statistical processing of the obtained results. Additionally, it has been found that the method effects an extremely high correlation between values of the concentration obtained from the measurements. Hence, the determining of the concentration may comprise comparison and cross-validation of the results obtained from the two or more measurements. The comparison and cross-validation may include the calculation of the average and a statistical procedure of standard deviation values. Information about a statistical error in a specific measurement may be of a great importance for a physician or a customer.

Values of concentrations obtained by the novel method can also be used for cross-validation of results obtained by the regular AC technique, such as pulse oximetry, i.e., for evaluating reliability of these results.

The method is preferably intended for measuring the concentration of chemical or biological substances which are present in the blood, regardless of the character of its flow. It should, however, be noted that the method can also be used for determining blood oxygen saturation and/or other parameters that depend on the existence of a normal blood pulse, provided additional conditions and approximations are taken into consideration.

The inventive method can be used both for independent measurements and for calibration of other non-invasive methods intended for obtaining similar data and based on measurements synchronized with the blood pulse, for example, methods for the continuous monitoring of blood parameters at departments of intensive care in hospitals.

There is also provided, according to another aspect of the present invention, an optical measurement system for non-invasive determination of concentration of at least one substance in blood, the system comprising:

an illumination-detection arrangement for attaching to a patient's blood perfused fleshy medium, the illumination-detection arrangement being designed to illuminate the medium with at least two different wavelengths of incident light, detect light response of the illuminated medium and generate data representative thereof;

a pressurizing assembly capable of applying an over-systolic pressure to the blood perfused fleshy medium with the normal blood flow; and     a control unit interconnected between said illumination-detection arrangement and said pressurizing assembly, wherein         said control unit operates the pressurizing assembly so as to selectively apply the over-systolic pressure and cause a state of temporary blood flow cessation for a cessation time period being insufficient for irreversible changes in the fleshy medium, and release the over systolic pressure to cause a state of transitional blood flow terminating with the normal blood flow; and         said control unit operates the illumination-detection arrangement so as to take the optical measurements during at least two different moments such that light absorption of the medium at said at least two moments essentially differs from each other and at least one of said at least two moments is selected within a time period including the state of temporary blood flow cessation and the state of transitional blood flow, the control unit being responsive to said data representative the detect light response of the illuminated medium for analyzing said data and determining the concentration of said at least one substance of the blood.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
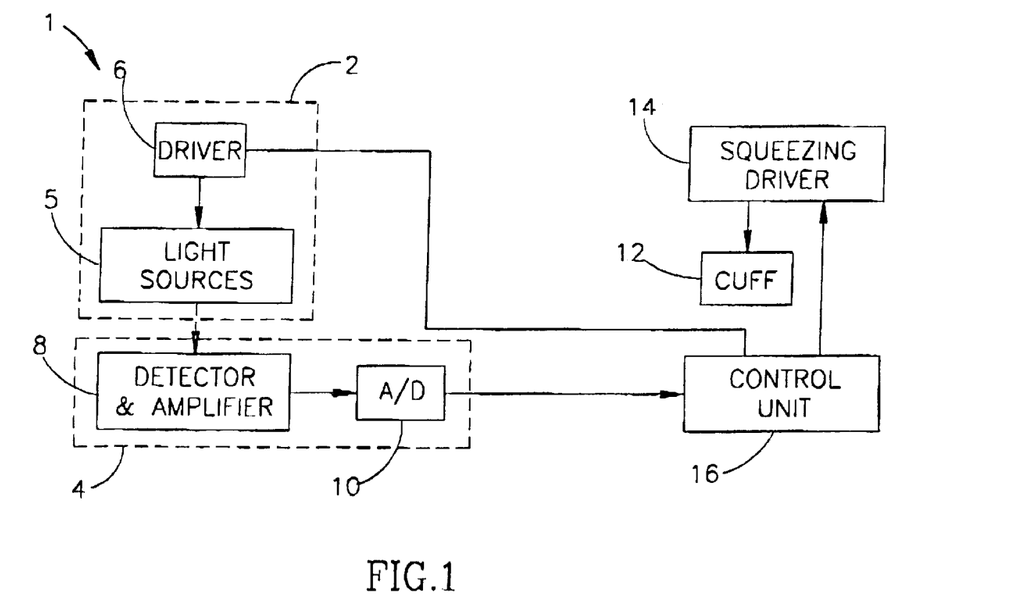
FIG. 1 is a schematic block diagram of the main components of a measuring apparatus according to the invention.

Referring to FIG. 1, there are illustrated the main components of a measuring apparatus 1, utilized for carrying out a method of the present invention. The apparatus 1 typically comprises such main constructional parts as an illumination assembly 2 and a detection assembly 4.

The illumination assembly 2 includes a plurality (an array) of light sources 5 associated with a suitable drive mechanism 6. The light sources generate incident radiation propagating through tissue at a measurement location.

The detection assembly 4 includes one or more detector 8 (typically equipped with an amplifying means) accommodated so as to detect either light transmitted through the tissue or light scattered (reflected) therefrom, as the case may be, and generating data representative thereof. The transmitted or reflected signal constitutes light response of the illuminated medium. The generated data is processed by a suitable analog to digital (A/D) converter 10 to provide digital output of the detection assembly 4.

Further provided in the apparatus 1 is a pressurizing assembly including a cuff 12 which may be of any known suitable type for attaching to the patient's fleshy medium (e.g. his finger), and a squeezing driver 14 that applies pressure to the location on the patient's tissue underneath the cuff 12. The squeezing driver 14 may also be of any known suitable type, for example that disclosed in a co-pending application assigned to the assignee of the present application.

It is important to note that the technique may be such that the pressure is applied at a first location on the fleshy medium, while the measurements are performed at a second location downward of the first location with respect to the direction of the blood flow. For example, the cuff 12 is accommodated on the patient's wrist or palm, and the illumination/detection assemblies are located at the patient's finger.

A control unit 16 is interconnected between the illumination and detection assemblies 2 and 4, and is coupled to the squeezing driver 14 (i.e., to the pressurizing assembly). The control unit 16 is thus responsive to the output of the detection assembly 4. It should be noted, although not specifically shown, that the control unit 16 is a computer device having such known utilities as a memory, a processor, a synchronizer, a display, etc. The processor is preprogrammed by suitable software capable of analyzing the received output of the detection assembly and determining one or more desired parameters of the patient's blood.

The construction and operation of all the above elements of the measuring apparatus are known per se and therefore need not be more specifically described, except to note the following. The control unit 16 selectively operates the pressurizing assembly to apply over-systolic pressure to the fleshy medium underneath the cuff 12 and release the pressure, so as to operate the illumination/detection assemblies to take measurements at different states of the blood flow, as will be described more specifically further below.

Figure 2:
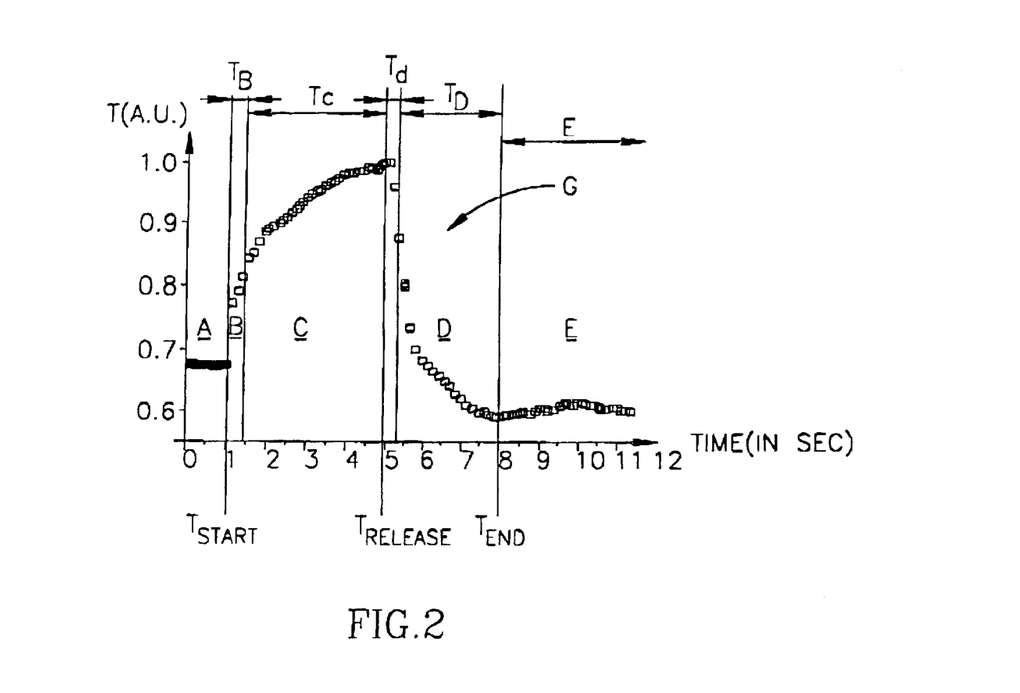
FIG. 2 illustrates a graph showing fluctuations of light transmitting characteristics of blood, which is experimentally obtained by applying the system of FIG. 1 to a fleshy medium.

FIG. 2 illustrates a graph G presenting experimental results obtained by applying the apparatus 1 to the patient's blood-perfused fleshy medium. The graph G shows how the light transmitting characteristic of blood changes under the application of an over-systolic pressure to the blood-perfused fleshy medium. In this specific example, the transmitting characteristic is a so-called Relative Transmission, i.e., Transmission arbitrary units or T(A.U.).

The application of pressure starts at a moment $T_{start}$, and is maintained for a period of time such as not to cause irreversible changes in the fleshy medium (e.g., 4 seconds). The pressure is released at the moment $T_{release}$. Measurements of the Relative Transmission are performed continuously starting prior to the application of the over-systolic pressure. Different states of the blood flow, designated A, B, C, D and E, are observed.

State A is a state of normal blood flow before the over-systolic pressure is applied. As shown, this state is characterized by a standard fluctuating value of the relative light transmission of blood.

State B starts at the moment $T_{start}$ (when the pressure is initially applied) and exists during a short period of time $T_B$ (about 0.5 sec) within which the over-systolic pressure is actually applied. Measurements taken during this time period should be disregarded due to the unavoidable influence of motional and/or other artifacts causing non-monotonic fluctuations of the light transmission.

State C is a state of the temporary cessation of blood flow which lasts within a time period $T_C$ between a moment determined as $(T_{start}+T_B)$ and the moment $T_{release}$. During this period of time $T_C$ the ascending curve (or descending curve depending on the incident wavelength) of relative light transmission of blood is observed, which reaches its maximum and may last for about 2–5.5 sec (generally, from one second to several minutes).

It is appreciated that when the over-systolic pressure is applied to any proximal part of the body, there is still sufficient space for the redistribution of blood between the exact area of the measurement (i.e. the location of the detector) and the adjacent areas in close proximity to the detector. For example, if the detector is located on a fingertip and the over-systolic pressure is applied on the palm, there is enough space between the fingertip and the margin of the applied pressure to "squeeze" the blood from one location to another.

State D is a transitional state of blood flow which takes place after releasing the over-systolic pressure. This state starts with a slight delay $T_d$ (approximately 0.5 sec), i.e. at the moment determined as $(T_{release}+T_d)$. During the time period $T_D$ of the duration of state D the relative transmission of blood monotonously descends until it reaches values characteristic of the normal blood flow. Such a moment is marked as $T_{end}$ in the drawing.

The end of state D, and the beginning of state E, is detected when the changes of the light transmission become periodic and minimal (about 2%). State E is a state of normal blood flow, which is similar to state A.

To carry out the method according to the invention, at least two timely-separated sessions of non-invasive optical measurements should be effected. These two measurement sessions may be taken during the following states of the blood flow: A and C; C and C; C and D; D and D; C and E; D and E. In other words, at least one of these at least two sessions is always taken during either the state C of temporary cessation of the blood flow, or the state D of transitional blood flow, i.e., within a time period including these two states $(T_C+T_D)$.

Figure 3:
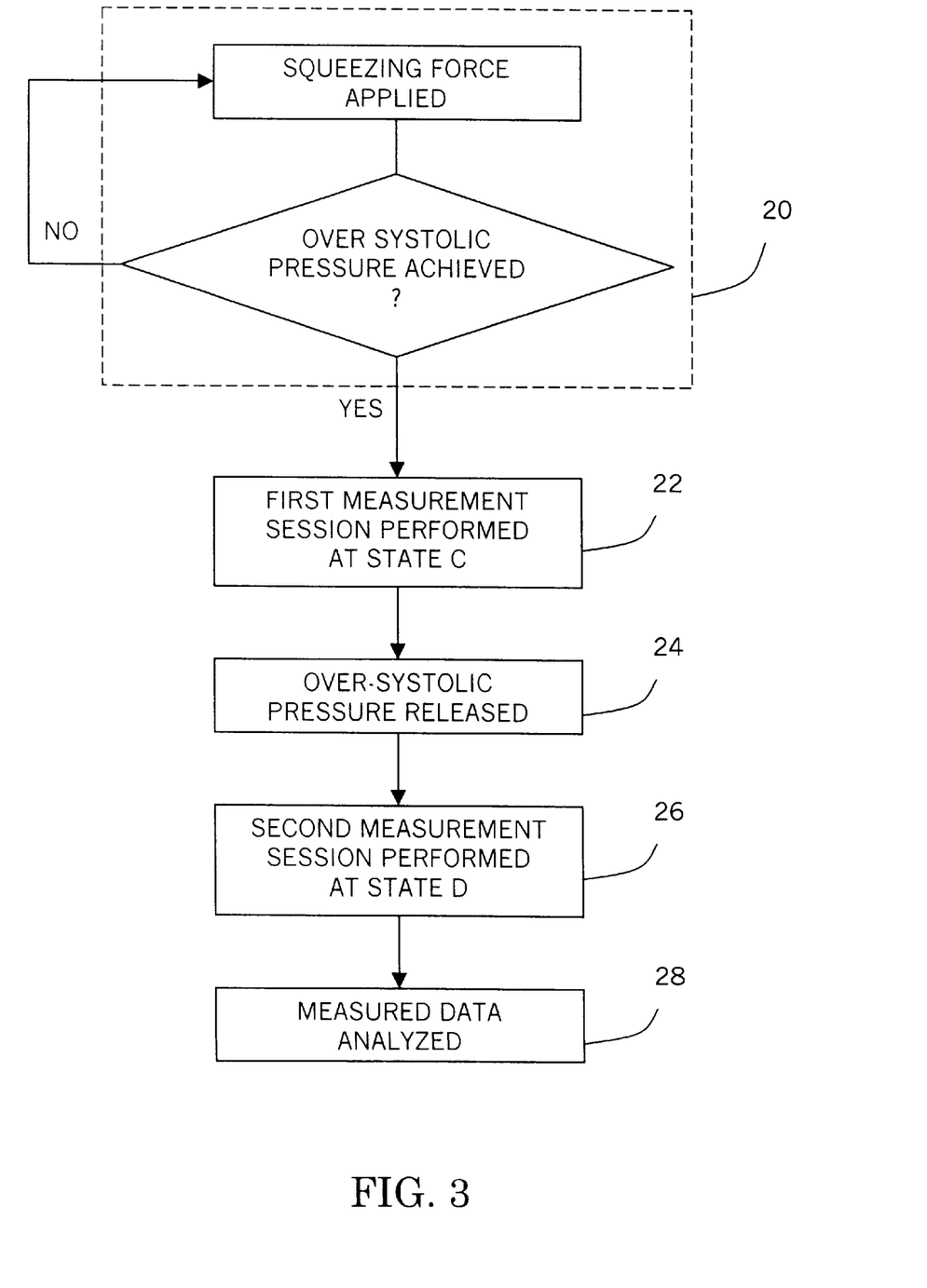
FIG. 3 is a flow diagram of the main operational steps in a method of the present inventive.

FIG. 3 illustrates a schematic flow diagram of the main operational steps of one possible example of the method according to the invention. In his example, the two measurements are taken at the states C and D, respectively. To this end, the following operational steps are performed:

Step 20: Over-systolic pressure of about 220 mmHg is applied to a proximal area of a human body, such as a fingertip, by applying a squeezing force created in the cuff 12. Duration of this operational step is about 0.5 sec.

Step 22: A first session of a non-invasive optical measurement is effected at the state of temporary cessation of blood flow (i.e., state C), when the changes of relative light transmission are monotonous (time-dependent) and positive. The measurement is actuated by the control unit 16. More specifically, the light sources are operated, and the fingertip is irradiated by different wavelengths. Light signals coming from the fingertip are detected, amplified and, after being converted into the digital form, are transmitted to the control unit 16, where they are stored and further processed. During the first session, whose duration is about 5 sec, the control unit 16 operates to maintain the cuff 12 in its squeezed position.

Thus, the results of a number of different measurements (i.e., with different wavelengths) taken during the first session are stored as $S_1(w,t)$. Here, S is the spectral intensity, w is the wavelength and t is the time. The concentration value $C_1$, for example of hemoglobin, is calculated from the $S_1(w,t)$, in a manner described further below.

Step 24: The control unit 16 operates the pressurizing assembly to release the over-systolic pressure. The squeezing action of the cuff 12 is ceased, and after a short delay of about 0.5 sec the blood flow gradually increases during approximately 5 sec.

Step 26: The control unit 16 actuates a second session of the non-invasive optical measurements to be effected at the state D of the transitional blood flow. The light sources continue to illuminate the fingertip, but the squeezing is halted. The detectors being synchronized by the control unit 16 detect light signals coming from the fingertip, and the digital output, $S_2(w,t)$, is received at the control unit 16. The concentration value $C_2$ of hemoglobin is calculated from $S_2(w,t)$ in a manner described further below.

Step 28: Now, the processor of the control unit 16 operates to analyze the calculated values $C_1$ and $C_2$ based, for example, on a statistical analysis performing the comparison and cross-validation of the calculated values. The resulting concentration C is obtained and displayed on the display of the control unit 16.

The results $S_1(w,t)$ and $S_2(w,t)$ obtained at, respectively, the first and second sessions of the measurements can be processed to find k concentrations $C_1$ to $C_k$ of k substances in blood using a specific procedure, which may, for example, consist of the following:

As indicated above, on the one hand, each of the data $S_1(w,t)$ and $S_2(w,t)$ represents a plurality of readings of spectral measurements on the fleshy medium. On the other hand, each of these data is a function of the variables w and t, where t is the time and w is the wavelength.

Assume that the time-dependence of the blood absorption spectrum can be described by:

$$S(w,t) = So(w) * \exp(-f(t) * S_1(w))$$

where $So(w)$ is a DC (constant) component of the spectrum intensity, $f(t)$ gives the shape of the time-dependent signal, and $S_1(w)$ gives an AC part (variable) of the spectrum, i.e.

$$S_1(w) = \sum_k C_k \mu_k(w)$$

Here, $\mu_k(w)$ is the absorption coefficient of k-th component (which is known), and $C_k$ is its concentration which is to be found.

Concentrations of k components are given in relative units, as follows:

$$\sum_k C_k = 1$$

To reconstruct the desired concentrations, the following simple procedure can be made:

$$\text{Log} \frac{S(w,t)}{S*(w,t_0)} \equiv z(w,t) = \sum_k \mu_k(w) y_k(t)$$

where $y_k = (f(t)-f(t_o))C_k$; $S*(w,t_o)$ is a so-called reference point (with respect to a DC level); $y_k$ is a factor associated with the contribution of the corresponding $C_k$ component to the optical signal change; $z(w,t)$ is the function of absorption of the AC-component of the measured optical signal. There are N unknown values of $y_k$ (N $\leq$ the number of spectral points of interest.

Using a well-known method of Least Squares (so-called "LS method"), the most suitable values of $y_k$ can be derived, after which values of the concentration $C_k$ can be determined as follows:

$$C_k = y_k(t) \bigg/ \sum_k y_k(t).$$

It should be noted that the method according to the invention may utilize any other suitable mathematical procedure for statistical analysis and reconstruction of the desired concentrations.

It should also be noted that the above technique refers to both of the following cases:

(1) one of the at least two measurements is taken at a normal blood flow state, and the other one is taken during the period including the temporary cessation blood flow state and the transitional blood flow state (excluding two short time periods when the application of the over-systolic pressure is mechanically started and ceased causing non-monotonic fluctuations);

(2) both of these at least two measurements are taken during the period including the temporary cessation and the transitional blood flow states (similarly, excluding the short time periods when the application of the over-systolic pressure is started and ceased).

It has been found by the inventors, that the allowed duration of the temporary blood cessation state (state C) depends on many factors, and can be observed approximately between the moments of 0.5 sec and several minutes from applying the over-systolic pressure. If the changes of the light response (i.e., transmission or reflection) exceed 15–20%, the duration of the temporary blood cessation state may be shortened to 2–3 sec, after which the over-systolic pressure should be released.

Other measurements may be taken during the transitional blood flow (state D), which starts after the release of the over-systolic pressure (with a short delay caused by the mechanical character of the action) and lasts until the normal blood flow is established. The duration of the state of transitional blood flow depends, for example, on the volume of the fleshy medium under measurement, and may last, for example, from 5 to 6 seconds. The non-invasive optical measurements at the state of normal blood flow may last longer, but a period of about 2 to 5 seconds would be fairly sufficient.

The above data is given for measurements effected on a fingertip constituting a fleshy medium. Of course, deviations are possible if other body parts are considered, such as palms or toes in which it is easy to achieve a temporary cessation of the blood flow. The substance of interest may be glucose, hemoglobin, drugs, cholesterol, etc.

The method according to the invention actually presents a so-called "occlusion-release" (OR) measuring technique. To facilitate even more the understanding of the advantageous features of the present invention, the following should be considered.

Oxygen saturation is defined as the ratio of the content of oxyhemoglobin to the total amount of hemoglobin in the blood volume unit. Assuming that only two types of hemoglobin exist in the blood, namely oxyhemoglobin and reduced hemoglobin, the classic pulse oximetry method allows for determining the oxygen saturation. This method utilizes the so-called "natural pulsatile" component of a light transmission signal. This pure natural pulse-related signal component of a detected signal, determined by an appropriate signal processing technique is commonly called the "AC component" of the detected signal, whereas the entire transmission signal by itself is called the "DC component" of the detected signal.

The transmission measurements in the pulse oximetry are carried out simultaneously at two different wavelengths, for example $L_1$=760 nm and $L_2$=940 nm, where the significant difference in the light absorption of oxyhemoglobin and hemoglobin exists between the two chosen wavelengths. Two pairs of AC and DC components are obtained. Generally, the ratio R, defined as $(AC/DC)_{L1}/(AC/DC)_{L2}$, is the value of oxygen saturation. For example, using the above values of $L_1$ and $L_2$, the ratio R is equal to 0.69, which corresponds to the oxygen saturation of 97% (i.e., the normal arterial blood saturation).

The following example demonstrates how the method of the present invention enables the determination of a new value having the same meaning as the above ratio R, but using the methodology of the occlusion-release (OR) technique. This method of signal processing is applicable both in a commonly used pulse oximetry and in the OR technique, and may be called a "parametric slope" (PS) method.

EXAMPLE 1

Measurements are performed at two wavelengths $L_1$=760 nm and $L_2$=940 nm with the duration of real transmission about 85 seconds. For the purpose, commonly used LEDs with the radiation picks at 940 nm and 760 nm are employed.

Figure 4A:
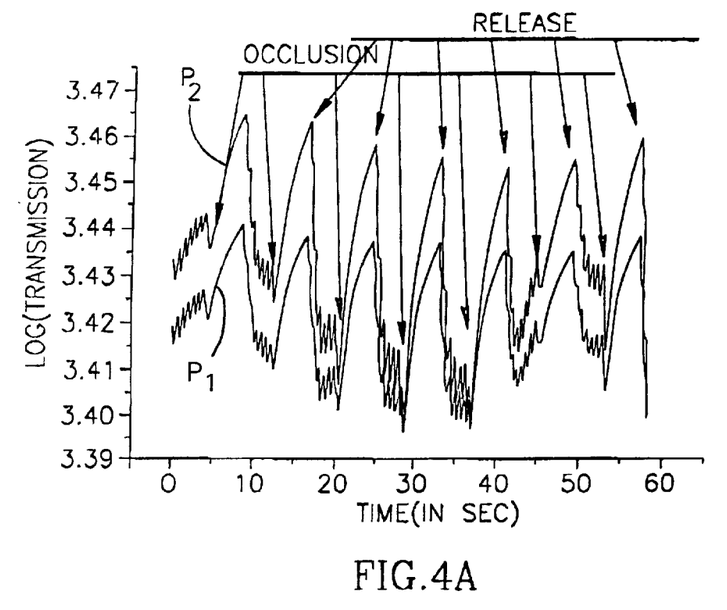
FIGS. 4a to 4d graphically illustrate various experimental results.

The entire measurement procedure consists of a single four-seconds standard pulsatile measurement interval and seven successive OR sessions. The transmission logarithms as functions of time are obtained. This is illustrated in FIG. 4a showing two graphs $P_1$ and $P_2$ corresponding to the wavelengths $L_1$ and $L_2$, respectively.

Figure 4B:
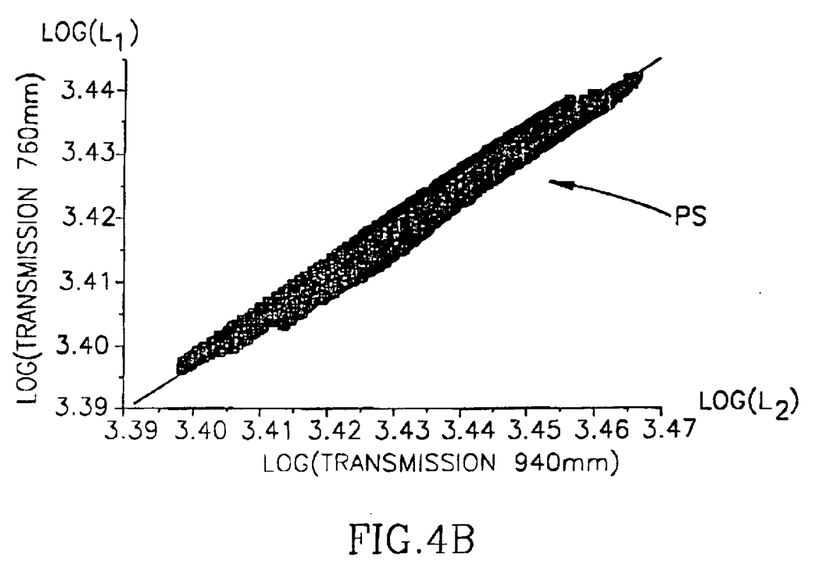

As illustrated in FIG. 4b, at a next stage, a parametric slope PS is plotted, as the transmission logarithm at the wavelength $L_2$, i.e., $\text{Log}(L_2)$, versus the transmission logarithm at the wavelength $L_1$, i.e., $\text{Log}(L_1)$, over the entire time interval (i.e., 85 seconds). In other words, the graph PS is a linear function of $\text{Log}(L_2)$ versus $\text{Log}(L_1)$. To determine the slope of this linear function, for example, a known linear regression algorithm can be used.

In this specific example of wavelengths and time parameters, the PS was found to be 0.69. The values of PS are determined at each one of the seven OR sessions, and even at each occlusion and each release session only. The average of all the PS values so obtained is around 0.69. This is illustrated in FIGS. 4c and 4d.

Figure 4C:
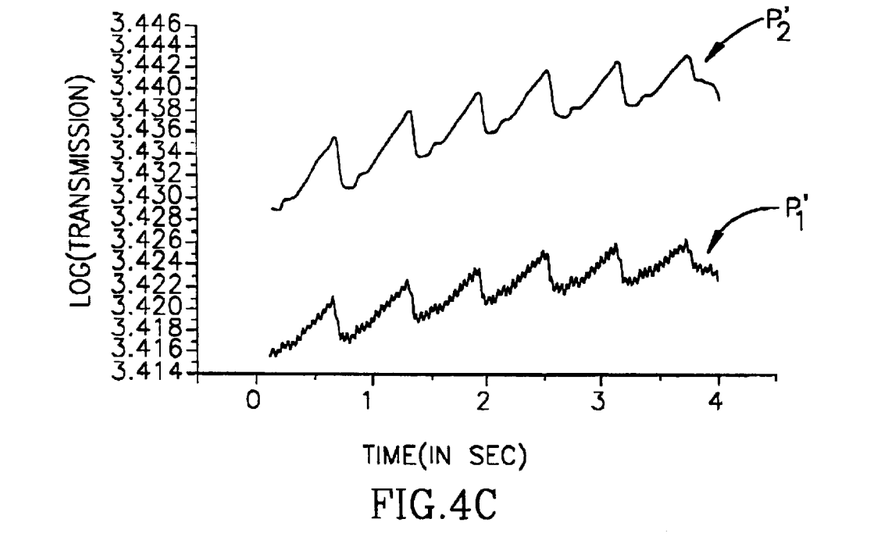

FIG. 4c presents graphs $P'_1$ and $P'_2$ showing only the pulsatile components of the transmission logarithms as functions of time corresponding to the wavelengths $L_1$ and $L_2$, respectively. These graphs $P'_1$ and $P'_2$ present the situation within the first four seconds of the entire measurement.

Figure 4D:
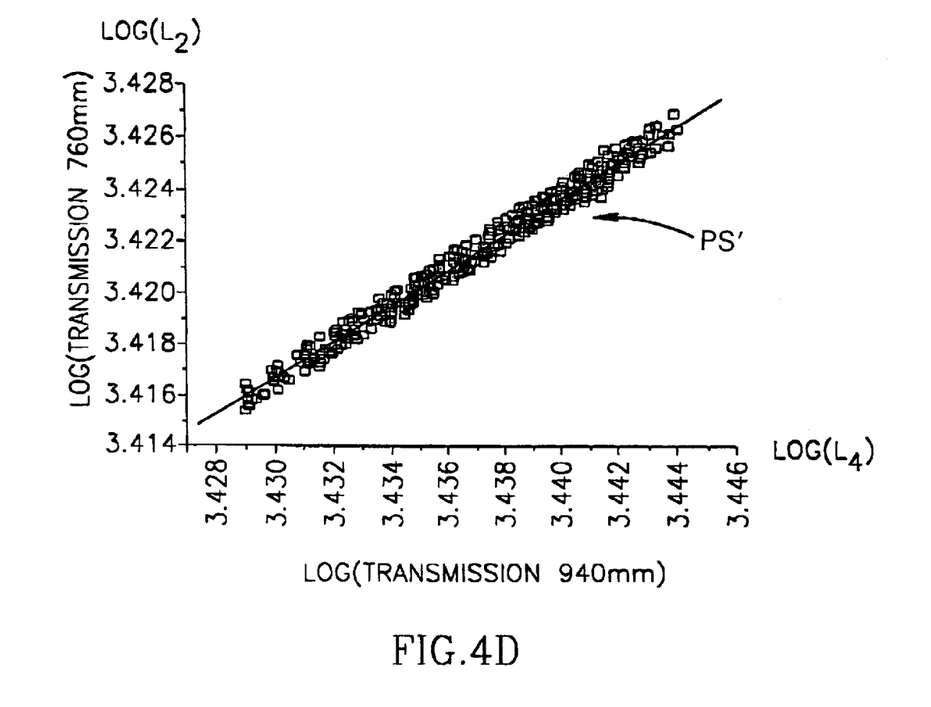

FIG. 4d illustrates a graph PS' presenting the transmission logarithm at the wavelength $L_2$ (760 nm) versus the transmission logarithm at the wavelength $L_1$ (940 nm) over the entire time interval (i.e., 85 seconds) obtained from the data in graphs $P'_1$, and $P'_2$. The PS' is found to be 0.69.

Thus, the application of the commonly used procedure for the pulsatile component to determine the ratio R reveals the same result. The accuracy of the determination of PS can be improved by performing a suitable pre-processing at each session of treatment This preprocessing procedure may, for example, be a low-pass digital filtration of a signal.

It is shown that the meaning of the PS parameter is the same as that of the R parameter. This means that the PS parameter can be used for oxygen saturation determination as well.

The advantage of the OR methodology for the oxygen saturation determination over the pulsatile is evident. Indeed, points where the significant pulsatile signal is not achieved, the much more noticeable OR signal can be achieved providing the desirable result.

The situation when the pulsatile signal is too weak to be detectable occurs during anesthesia, shock, low pressure, low temperature and other pulse compromising clinical situations. The most popular example of this situation is associated with a cardiology surgery where the patient's heart is temporarily disconnected from the physiological system, and only an extracorporal pump is responsible for the blood flow. In this situation, the pulsatile component is not detectable at all, and only the OR technique can provide the physician with the oxygen saturation values.

Obviously, the method described above can be similarly applied for the determination of glucose, hemoglobin, cholesterol, drugs and other analytes, only by changing the range of wavelengths of the incident radiation.

The experimental results have shown that the optical properties of blood can be significantly modulated by simply preventing the blood from flowing. Not only the changes of the optical properties of blood can be observed during the process of blood flow secession, but also the evolution of a very prolonged (continuing more then one minute) process of light transmission changes. These changes are not necessarily volumetric changes, but more likely are non-volumetric, and various kinds on information may be derived therefrom.

Following are two more examples showing the light transmission changes measured, respectively, in the in vitro experiments (in a transparent cuvette with rigid glass walls) and in the in vivo experiments (on the patient's fingertip). The same optical apparatus is used for these measurements.

EXAMPLE 2

Figure 5A:
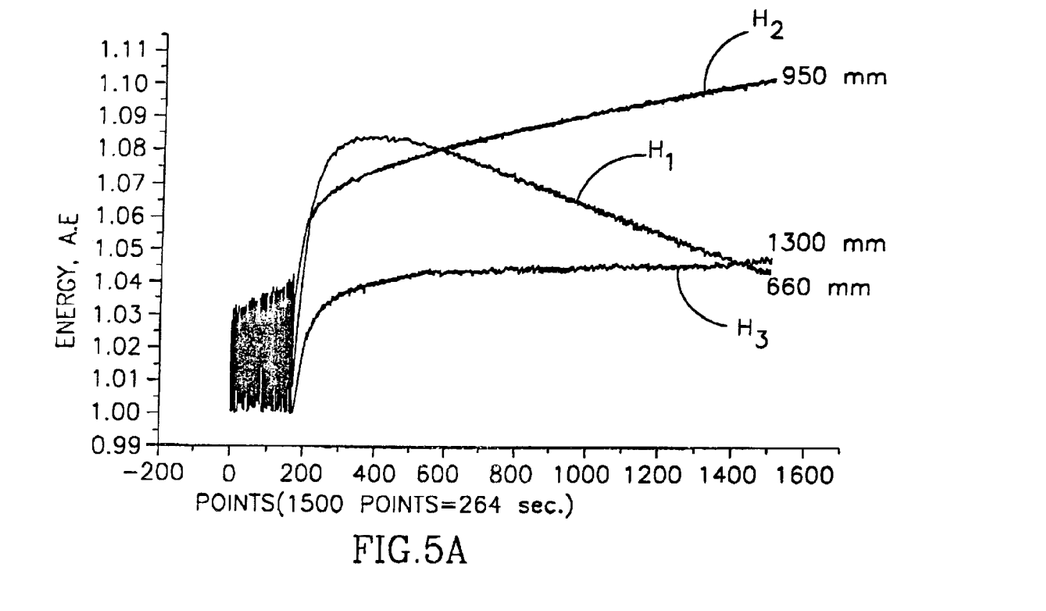
FIGS. 5a and 5b graphically illustrate experimental results relating, respectively, to in vitro and in vivo applications of the present invention.

The entire amount of human blood was pumped by peristaltic pump through a transparent cuvette with rigid glass walls. Immediately after the secession of a blood flow, the light transmission effect at different wavelengths started to change. This is illustrated in FIG. 5a showing three curves $H_1$, $H_2$ and $H_3$ corresponding to the wavelengths $L_1$=660 nm, $L_2$=950 nm and $L_3$=1300 nm, respectively. With restarting the blood flow, the transmission values return to their initial level.

It should be noted that, if the cuvette's walls are flexible, which actually presents a volumetric model, the transmission level gradually decreases at all of the above wavelengths. However, the avoidance of the volumetric effect leads to very peculiar transmission behavior, where the light transmission curves at different wavelengths vary differently, in course of the time.

EXAMPLE 3

Figure 5B:
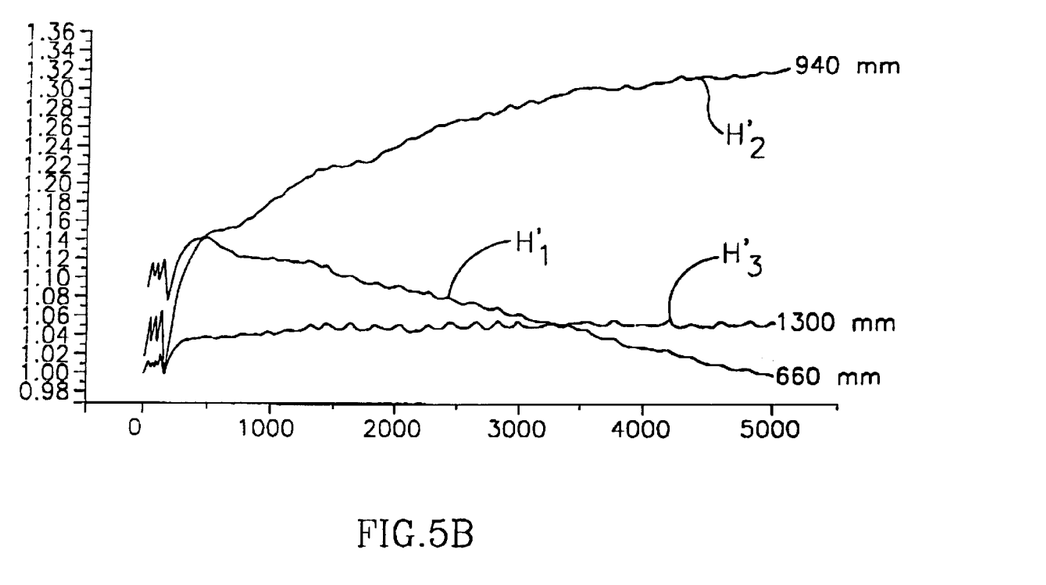

To stop the blood flow, the over systolic pressure is applied to the upper limb of a patient. Transmission behavior patterns, similar to those of the above-described In vitro experiments, are observed. This is illustrated in FIG. 5b showing three curves $H'_1$, $H'_2$ and $H'_3$ corresponding to the wavelengths $L_1$=660 nm, $L_2$=950 nm and $L_3$=1300 nm, respectively.

Both the time constants of transmission changes and the trends of these changes at different wavelengths were found to be very similar. Additionally, it was found that the results do not depend on the location of pressurizing, and do not depend on whether it is the upper finger, the wrist or the upper limb.

Thus, the advantages of the present invention are self-evident. Indeed, all the above experiments have shown that the application of the over-systolic pressure triggers the internal, non-volumetric mechanism in blood. This mechanism leads to continuous and gradual changes in the optical properties of the blood. These changes can be observed and recorded in immediate response to the application of the blood arresting pressure, or not long after this application. The results of these changes do not depend on any transient tissue-related local changes at the location of measurement. These changes can be considered as the solely blood-related ones, and can be utilized for the determination of various blood-related parameters.

Those skilled in the art will readily appreciate that various modifications and changes may be applied to the preferred embodiment of the invention as hereinbefore exemplified without departing from its scope defined in and by the appended claims. In the method claims which follow, characters which are used to designate claim steps are provided for convenience only and do not apply any particular order of performing the steps.

What is claimed is:

1. A non-invasive method of optical measurements for determining the concentration of at least one substance in patient's blood, the method comprising the steps of:
   (a) applying an over-systolic pressure to the patient's blood perfused fleshy medium with a normal blood flow at a first location on the patient's body, such as to cause a state of temporary blood flow cessation at a second location on the patient's body located downstream of said first location with respect to a normal blood flow direction for a cessation time period being insufficient for irreversible changes in the fleshy medium;
   (b) releasing the over systolic pressure at the first location to cause a state of transitional blood flow terminating with the normal blood flow at the second location;
   (c) selecting at least two timely separated sessions for performing the optical measurements on the blood perfused fleshy medium at said second location, wherein the selected sessions are such that light response of the medium at said at least two sessions substantially differs from each other, at least one of said at least two sessions being selected within a time period including the state of temporary blood flow cessation and the state of transitional blood flow, wherein said selecting includes distinguishing the normal blood flow from the state of temporary blood cessation by detecting that at least one optical characteristic associated with the light response of the blood has changed by a predetermined threshold value, and that the character of its change corresponds to a time-dependent function;

(d) effecting the measurements at said at least two sessions successively, each session including illumination of the second location with at least two different wavelengths of incident light and detection of light responses of the medium; and (e) determining for each of said at least two sessions a corresponding value of the concentration of said at least one substance, analyzing the determined values and obtaining a corrected value of said concentration.

2. The method according to claim 1, wherein each of said at least two sessions of the optical measurements is selected during a period of time including said state of temporary blood flow cessation and said state of transitional blood flow.

3. The method according to claim 1, wherein one of said at least two sessions is selected at a state of the normal blood flow.

4. The method according to claim 1, comprising effecting at least one additional measurement session for further statistical processing of the obtained results.

5. The method according to claim 1, wherein the analyzing of the determined values of the concentration comprises comparison and cross-validation of the results obtained from the said at least two sessions of measurements.

6. The method according to claim 5, wherein the comparison and cross-validation includes calculation of an average value of the concentration and statistical processing of standard deviation values.

7. The method according to claim 1, which serves for cross-validation of results obtained by an AC technique.

8. The method according to claim 1, which serves for cross-validation of results obtained for calibration of an AC technique.

9. The method according to claim 1, wherein duration of the temporary blood flow cessation state is in a range from one second to several minutes.

10. The method according to claim 1, wherein said at least one substance is glucose.

11. The method according to claim 1, wherein said at least one substance is hemoglobin.

12. The method according to claim 1, wherein said at least one substance is drug.

13. The method according to claim 1, wherein said at least one substance is cholesterol.

14. A non-invasive method of optical measurements for determining concentration of at least one substance in the patient's blood, the method comprising the steps of:

(a) applying an over-systolic pressure to the patient's blood perfused fleshy medium with a normal blood flow at a first location on the patient's body, such as to cause a state of temporary blood flow cessation at a second location on the patient's body located downstream of said first location with respect to a normal blood flow direction for a cessation time period being insufficient for irreversible changes in the fleshy medium.

(b) releasing the over systolic pressure at the first location to cause a state of transitional blood flow terminating with the normal blood flow at the second location;

(c) selecting at least two timely separated sessions for performing the optical measurements on the blood perfused fleshy medium at said second location, wherein the selected sessions are such that light response of the medium at said at least two sessions substantially differs from each other, at least one of said at least two sessions being selected within a time period including the state of temporary blood flow cessation and the state of transitional blood flow;

(d) effecting the optical measurements at said at least two sessions successively, each session including illumination of said second location with first and second wavelengths of incident light, and detection of first and second light responses of the medium;

(e) determining a logarithm of the detected light response at the first wavelength as a function of a logarithm of the detected light response at the second wavelength; and (f) determining the concentration as a parametric slope of said function.

15. The method according to claim 14, wherein said determining of the concentration utilizes a linear regression algorithm.

16. The method according to claim 1, wherein the patient's heart is temporarily disconnected from the physiological system, and an extracorporal pump is responsible for the blood flow.

17. An optical measurement system for non-invasive determination of concentration of at least one substance in the patient's blood, the system comprising:

(a) a pressurizing assembly operable for applying an over-systolic pressure to the blood perfused fleshy medium with the normal blood flow at a first location on the patient's body to thereby create a state of temporary blood flow cessation at a second location on the body downstream of said first location with respect to a normal blood flow direction, while substantially not affecting blood volume at the second location;

(b) an illumination-detection arrangement operable to illuminate the medium at said second location with at least two different wavelengths of incident light, detect light responses of the illuminated medium and generate data representative thereof; and (c) a control unit interconnected between said illumination-detection arrangement and said pressurizing assembly, wherein said control unit operates the presurizing assembly so as to selectively apply the over-systolic pressure to the first location and thereby create the state of temporary blood flow cessation at the second location, maintain the over systolic pressure at the first location for a cessation time period being insufficient for irreversible changes in the fleshy medium, and release the over systolic pressure at the first location to create a state of transitional blood flow terminating with the normal blood flow at said second location; and said control unit operates the illumination-detection arrangement to perform the optical measurements during at least two timely separated measurement sessions, each with said at least two different wavelengths of the incident light, the measurement sessions being selected such that the light responses of the medium to the incident light of the same wavelength at said at least two sessions substantially differ from each other, and at least one of said at least two sessions is selected within a time period including the state of temporary blood flow cessation and the state of transitional blood flow;

said control unit is responsive to said data representative of the detected light responses to define measurement results in the form of the at least two light responses as different functions of time corresponding to the at least two different wavelengths, respectively, and to analyze the measurement results and determine relation between the two functions indicative of the concentration of said at least one substance of the blood.

18. A non-invasive method of optical measurements for determining concentration of at least one substance in patient's blood, the method comprising the steps of:
(a) applying an over-systolic pressure to the patient's blood perfused fleshy medium with a normal blood flow at a first location on the patient's body, thereby creating a state of temporary blood flow cessation at a second location on the body downstream of the first location with respect to a normal blood flow direction, while substantially not affecting blood volume at the second location, and maintaining the pressure to maintain the blood flow cessation state for a cessation time period being insufficient for irreversible changes in the fleshy medium;
(b) releasing the over systolic pressure at the first location thereby creating a state of transitional blood flow terminating with the normal blood flow at the second location;
(c) selecting at least two timely separated sessions for the optical measurements at said second location, wherein the selected sessions are such that light responses of the medium to incident light of the same wavelength at said at least two sessions substantially differ from each other, at least one of said at least two sessions being selected within a time period including the state of temporary blood flow cessation and the state of transitional blood flow;
(d) performing the optical measurements at said at least two sessions at said second location, each session including illumination of the second location with at least two different wavelengths of incident light and detection of light responses of the medium, thereby obtaining measurement results in the form of at least two light responses of the medium as different functions of time corresponding to said at least two wavelengths, respectively; and
(e) analyzing the measurement results to determine relation between the two time functions indicative of the concentration of said at least one substance.

19. The method according to claim 18, wherein said selecting of the at least two sessions comprises distinguishing the normal blood flow from the state of temporary blood cessation by detecting that at least one optical characteristic associated with the light response of the blood has charged by a predetermined threshold value, and that the character of tis change corresponds to a time-dependent function.

20. The method according to claim 19, wherein said at least one optical characteristic is indicative of the light transmission of the blood prerfused medium.

21. The method according to claim 19, wherein said at least one optical characteristic is indicative of the light reflection of the blood perfused medium.

22. The method according to claim 19, wherein the threshold difference between said at least two measurement sessions is about 5%.

23. The method according to claim 9, wherein duration of the temporary blood flow cessation is in a range from 2 seconds to 5.5 seconds.

24. The method according to claim 18, wherein step (e) comprises the steps of utilizing a time dependence of a blood absorption and scattering spectrum for each of said at least two measurement sessions and determining a corresponding value of the concentration; and analyzing the determined values of the concentration to determine a corrected value corresponding to the value of said concentration of the at least one substance in blood.

25. The method according to claim 18, wherein step (e) comprises the steps of determining a function corresponding to a ratio between the at least two time functions of the light response, and determining said concentration of the substance as a parametric slope of said function.

* * * * *

UNITED STATES PATENT AND TRADEMARK OFFICE
Certificate

Patent No. 6,400,972 B1

Patented: June 4, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Ilya Fine, Rehovot, IL; and Leonid Shvartsman, IL.

Signed and Sealed this Twentieth Day of May 2003.

MAX HINDENBURG
*Supervisory Patent Examiner*
Art Unit 3736